(12) United States Patent
Knecht et al.

(10) Patent No.: US 9,924,891 B2
(45) Date of Patent: Mar. 27, 2018

(54) METHOD OF PREPARING AN IMAGE FOR USE IN PRODUCTION OF A KNEE BRACE AND A TIBIAL CONTOUR GAUGE AND AN IMAGE ALIGNMENT GUIDE FOR USE IN SAID METHOD

(71) Applicant: Townsend Industries, Inc., Bakersfield, CA (US)

(72) Inventors: Steven S. Knecht, Gardnerville, NV (US); Frederic Desmoulins, Denver, CO (US)

(73) Assignee: Townsend Industries, Inc., Bakersfield, CA (US)

( * ) Notice: Subject to any disclaimer, the term of this patent is extended or adjusted under 35 U.S.C. 154(b) by 374 days.

(21) Appl. No.: 14/433,690

(22) PCT Filed: Oct. 2, 2013

(86) PCT No.: PCT/US2013/063004
§ 371 (c)(1),
(2) Date: Apr. 6, 2015

(87) PCT Pub. No.: WO2014/055614
PCT Pub. Date: Apr. 10, 2014

(65) Prior Publication Data
US 2015/0257678 A1    Sep. 17, 2015

Related U.S. Application Data

(60) Provisional application No. 61/709,635, filed on Oct. 4, 2012.

(51) Int. Cl.
*A61B 5/11*    (2006.01)
*A61B 5/107*    (2006.01)
(Continued)

(52) U.S. Cl.
CPC .......... *A61B 5/1079* (2013.01); *A61B 5/0013* (2013.01); *A61B 5/0077* (2013.01);
(Continued)

(58) Field of Classification Search
CPC .... A61B 5/1079; A61B 5/1075; A61B 5/1072
(Continued)

(56) References Cited

U.S. PATENT DOCUMENTS

| | | | |
|---|---|---|---|
| 1,268,002 A | | 5/1918 | Goodwin |
| 2,339,657 A | * | 1/1944 | Smith .................. A61B 5/1079 355/40 |

(Continued)

FOREIGN PATENT DOCUMENTS

WO    01/67957 A1    9/2001

*Primary Examiner* — Christopher Fulton
(74) *Attorney, Agent, or Firm* — David S. Safran

(57) ABSTRACT

An image alignment guide for producing images for producing a knee brace has an arm carrying a focal angle tube, a mechanism for positioning the arm against the lateral side of the leg of a patient, and a mechanism for setting the level of the brace. The guide is used in method of preparing such images involving taking images with the image alignment guide against the lateral side of a patient's leg at an anterior-posterior mid-line thereof with the focal angle tube at the side of the knee and at a distance therefrom, respectively, measuring the length of the patient's leg from the patella center to a position on the leg at which a shell of a brace to be produced is to be located, measuring the crest of the tibia using a tibial contour guide and sending all images, readings and measurements obtained to a knee brace manufacturer.

2 Claims, 13 Drawing Sheets

(51) Int. Cl.
*A61B 5/00* (2006.01)
*A61F 5/01* (2006.01)

(52) U.S. Cl.
CPC .......... *A61B 5/1071* (2013.01); *A61B 5/1072* (2013.01); *A61B 5/1075* (2013.01); *A61B 5/1077* (2013.01); *A61B 5/4585* (2013.01); *A61B 5/4836* (2013.01); *A61F 5/0123* (2013.01)

(58) Field of Classification Search
USPC ................................. 33/512, 561.1, 514.2
See application file for complete search history.

(56) References Cited

U.S. PATENT DOCUMENTS

| | | | | |
|---|---|---|---|---|
| 3,964,169 | A * | 6/1976 | Bush | A41H 1/02 33/15 |
| 4,662,079 | A * | 5/1987 | Graf | A43B 7/28 33/3 R |
| 4,819,660 | A * | 4/1989 | Smith | A61B 5/0064 33/515 |
| 4,974,331 | A * | 12/1990 | Watterson | A41H 1/02 33/15 |
| 5,148,606 | A | 9/1992 | Mason et al. | |
| 5,263,492 | A * | 11/1993 | Voyce | A61B 5/1071 33/471 |
| 5,457,891 | A | 10/1995 | Taylor | |
| 6,383,148 | B1 | 5/2002 | Pusch et al. | |
| 7,225,554 | B2 * | 6/2007 | Madsen | A61B 5/107 33/512 |
| 7,291,002 | B2 | 11/2007 | Russell et al. | |
| 7,756,325 | B2 | 7/2010 | Vetter et al. | |
| 8,119,053 | B1 | 2/2012 | Bedal et al. | |
| 8,175,734 | B2 | 5/2012 | Fogel et al. | |
| 8,881,417 | B2 * | 11/2014 | Sano | A61B 5/107 33/512 |
| 9,241,682 | B2 * | 1/2016 | Aram | A61B 6/5241 |
| 2004/0107592 | A1 * | 6/2004 | Matlis | A61B 5/1071 33/512 |
| 2014/0055590 | A1 * | 2/2014 | Smith | A61B 5/0082 348/77 |
| 2014/0063220 | A1 * | 3/2014 | Taylor | A61F 5/0106 348/77 |

* cited by examiner

METHOD OF PREPARING AN IMAGE FOR USE IN PRODUCTION OF A KNEE BRACE AND A TIBIAL CONTOUR GAUGE AND AN IMAGE ALIGNMENT GUIDE FOR USE IN SAID METHOD

CROSS REFERENCE TO RELATED APPLICATION

This application is a non-provisional conversion of provisional application 61/709,635, filed Oct. 4, 2012, 371 which is a PCT/US2013/063004 filed Oct. 2, 2013.

BACKGROUND OF THE INVENTION

Field of the Invention

The present invention relates to the field of custom knee braces and the manner in which such knee braces are produced in particular.

Description of Related Art

Custom knee braces, i.e., knee braces that have been made to fit a leg of a specific person, have been made have been made from a hand-modified positive model (filled cast) of a patient's leg. That is, to order a custom knee brace, the doctor would make a negative casting of the patient's leg and send it to the knee brace manufacturer with an order for the type of brace desired. The knee brace manufacturer would use the negative casting to make a positive model of the patient's leg to which the custom brace would be fit. There are significant costs associated with taking and shipping a cast mold, and with health insurance reimbursements declining and expenses increasing a need has arising for a less costly way of obtaining a custom knee brace.

In recent years, various devices for 3D printing of three dimensional solid objects from a digital model using additive processes have been developed. 3D printers create an object by laying down successive layers of material. The machine reads in data from a CAD drawing and lays down successive layers of liquid, powder, or sheet material, and in this way builds up the model from a series of cross sections. These layers, which correspond to the virtual cross section from the CAD model, are joined together or fused automatically to create the final shape. Examples of 3D printers can be found, e.g., in U.S. Pat. Nos. 8,175,734; 8,119,053; and 7,291,002 among very many others. This technology is used in the fields of jewelry, footwear, industrial design, architecture, engineering and construction (AEC), automotive, aerospace, dental and medical industries, education, geographic information systems, civil engineering, and many others. U.S. Pat. No. 7,756,325 discloses an algorithm for estimating the 3D shape of a 3-dimensional object, such as a human face, based on information retrieved from a single photograph by recovering parameters of a 3-dimensional model as well as methods and systems using same. Beside the pixel intensity, the invention uses various image features in a multi-features fitting algorithm (MFF) that has a wider radius of convergence and a higher level of precision and provides thereby better results. However, to date, a method of using 3D printer technology to create custom knee braces has not existed, at least in part, due to the lack of a means of obtaining a usable image.

SUMMARY OF THE INVENTION

The primary object of the present invention is to provide a method of producing a custom knee brace, and in connection therewith, a further object is to develop tools for use for use in preparing such an image.

The above objects are achieved in accordance with the present invention by the development of an image alignment guide that can be mounted to the patient's leg for which a custom brace is to be ordered, the guide providing a means for setting an ideal camera angle, and a tibial contour gauge that enables the medial and lateral angles of the patient's leg to be captured for use in accurately contouring the tibial shell of the brace.

The object is further achieved by a method in which an image alignment guide (IAG) is mounted to the lateral side of the patient's leg, side and frontal images of the leg art taken with the IAG on the leg, the IAG is removed and a tibial contour gauge (TCG) used to obtain readings of the medial and lateral angles, measuring of the circumference of the leg at several points, and sending the images, readings and measurements to the brace manufacturer for us in production of a knee brace.

DETAILED DESCRIPTION OF THE INVENTION

It is a primary object of the present invention to provide a method of producing digital images that are usable for producing a knee brace without the need to have the prescribing doctor prepare a positive model (filled cast) of a patient's leg and send it to the brace manufacturer for preparing of a model of the patient's leg, and to provide tools for use in such a process. While the method could be used with a commercially available 3D printer having the capability of producing an object of the size and shape of a knee brace, the method is not limited to such a method of knee brace production, which the current cost of such machines makes presently too expensive for use in the production of custom knee braces. Thus, currently the invention will find applicability with knee braces formed using malleable aluminum bands to create leg form on which graphite pre-preg is applied and cured.

Figure 1:
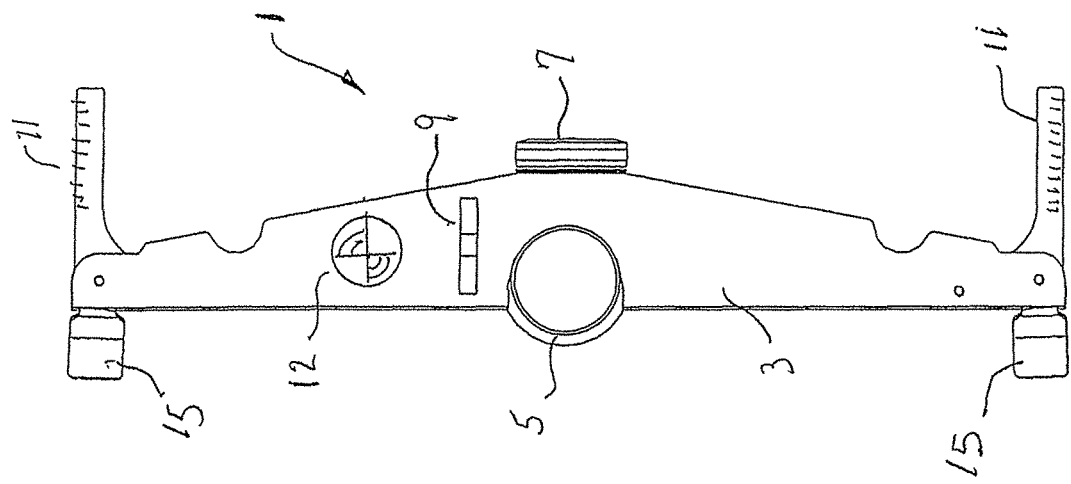
FIGS. 1-4 are front, inner side, outer side, back, and perspective views of an image alignment guide in accordance with the present invention.
Figure 2:
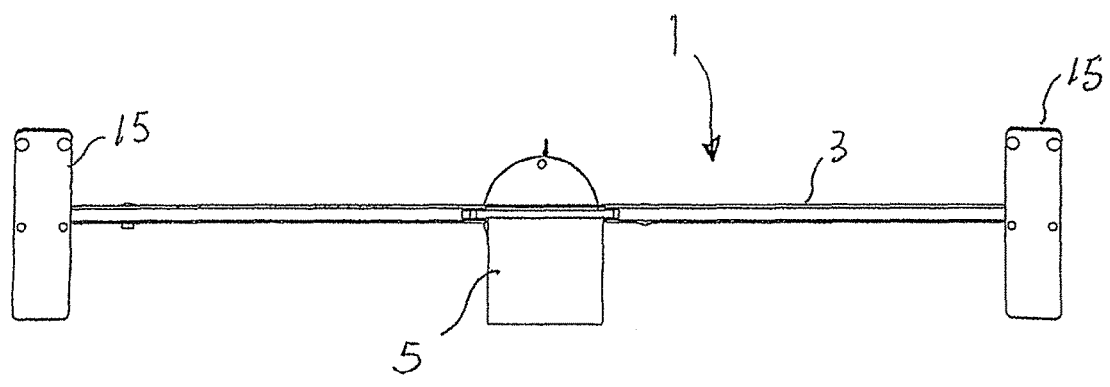
Figure 3:
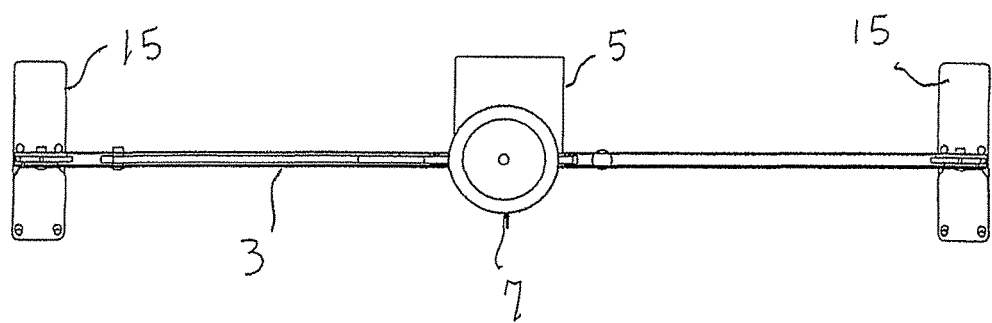
Figure 4:
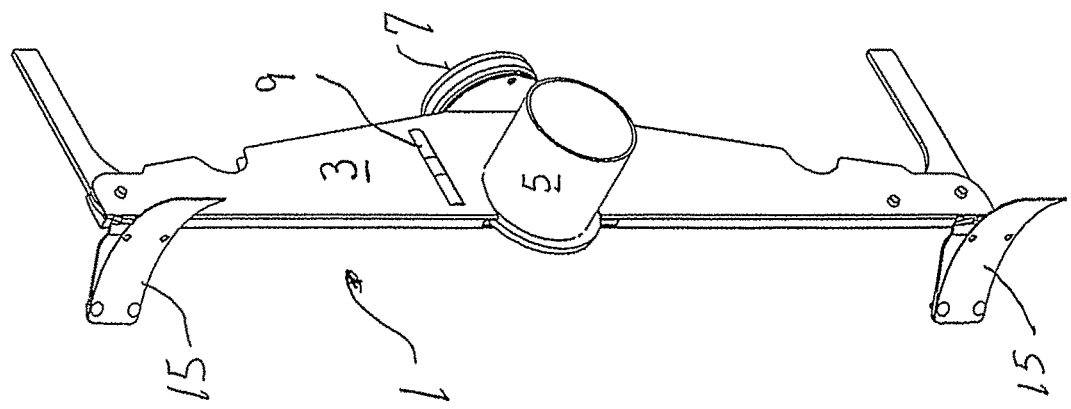
Figure 5:
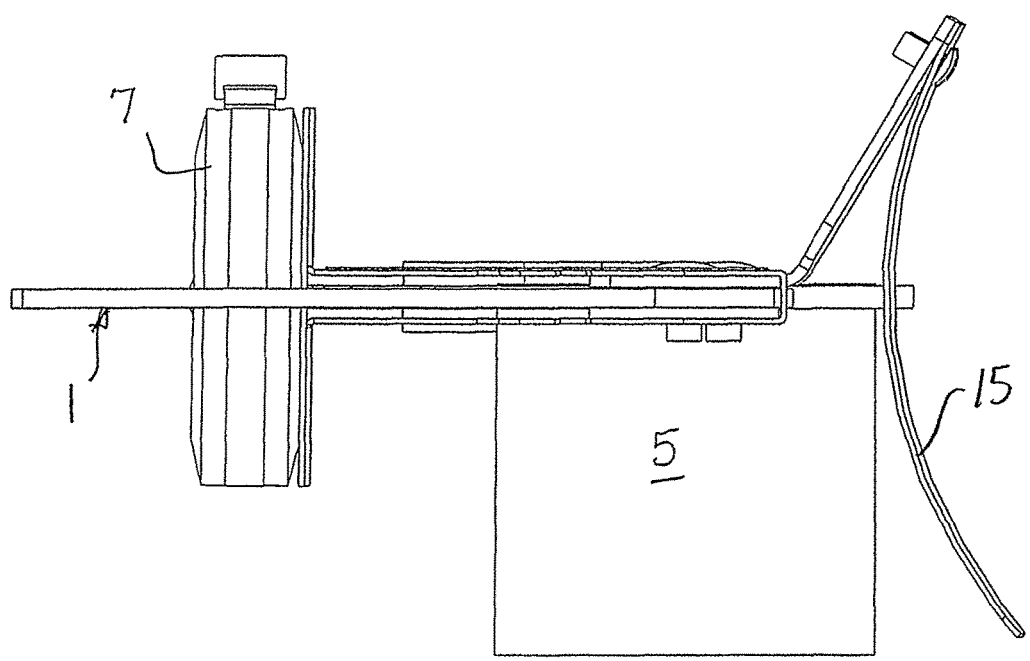
FIG. 5 is an enlarged view of an end portion of the image alignment guide shown in FIGS. 1-4.

FIGS. 1-4 are views of an image alignment guide (IAG) 1 in accordance with the present invention. The IAG 1 comprises an arm 3 that carries a focal angle tube 5, a removably mounted tape measure 7, a level 9, ruler arms 11, focusing element 12, and support arms 15, which are shown in greater detail in the enlarged view of an end portion of the IAG shown in FIG. 5. The purpose and use of the various parts of the IAG are explained below in connection with the method aspect of the invention.

Figure 6:
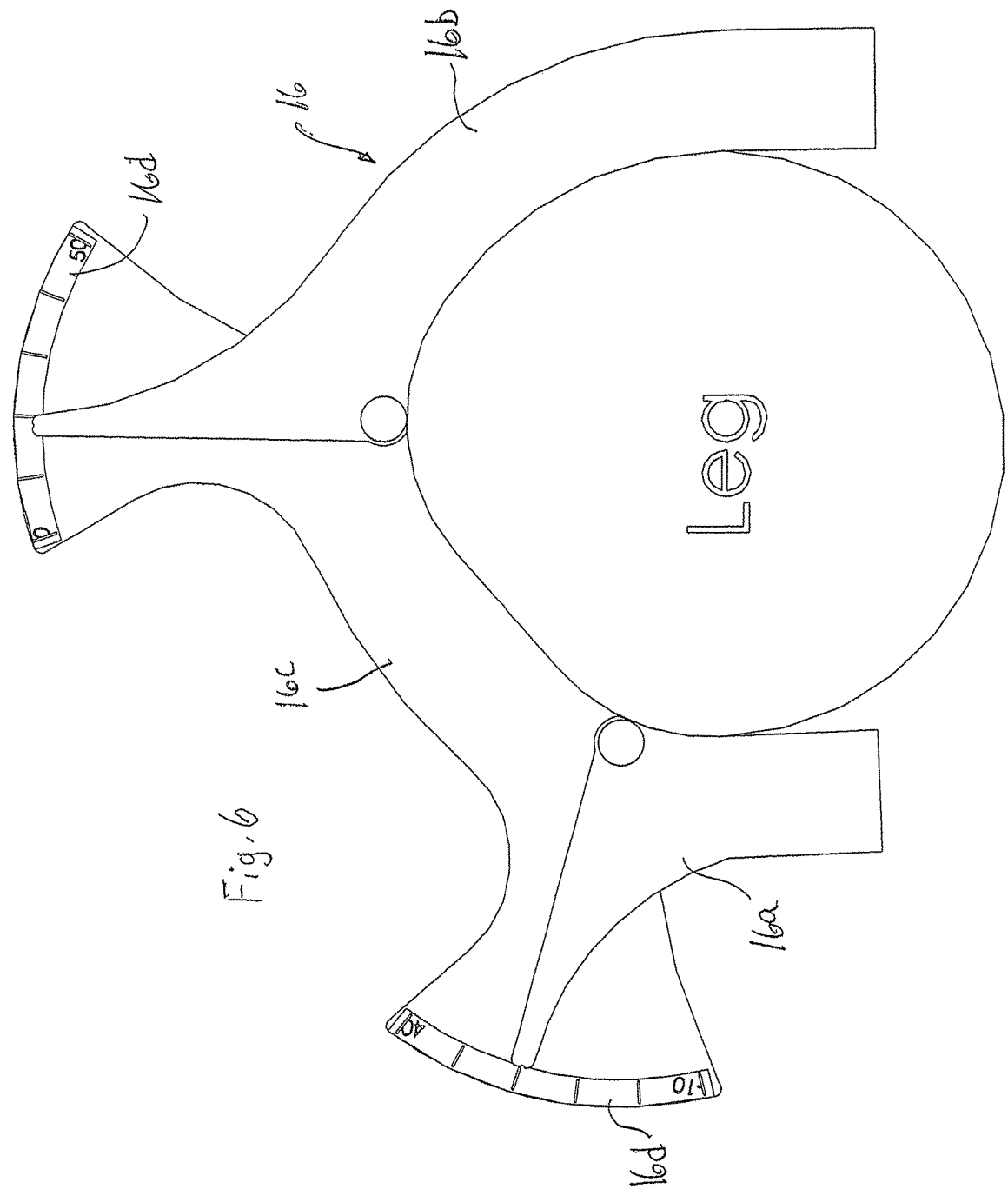
FIG. 6 is a front view of a tibial contour gauge in accordance with the present invention shown positioned a schematically depicted leg of a patient.

FIG. 6 is a front view of a tibial contour gauge 16 in accordance with the present invention shown positioned a schematically depicted leg of a patient. The tibial contour gauge 16 is formed of two indicator parts 16a, 16b that are pivotably mounted on a gauge part 16c, being pivoted out for use, and folded parallel with arm 3 for shipping. Here again, the purpose and use of the various parts of the tibial contour gauge are explained below in connection with the method aspect of the invention.

Figure 7:
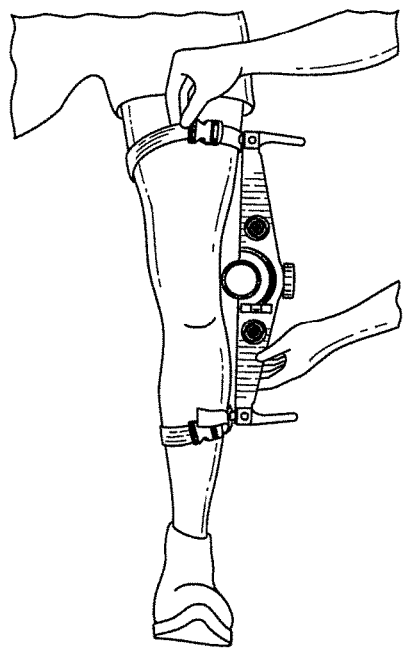
FIGS. 7-19 show steps in the performance of the method of the present invention.
Figure 8:
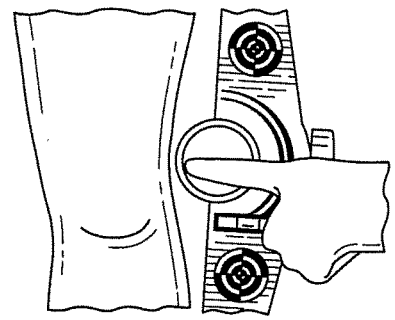
Figure 9:
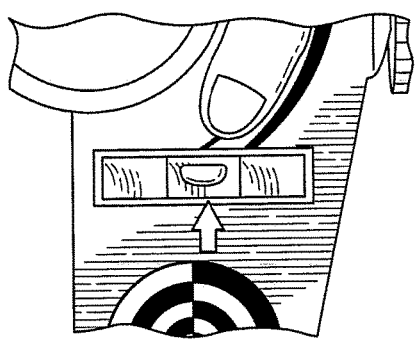
Figure 10:
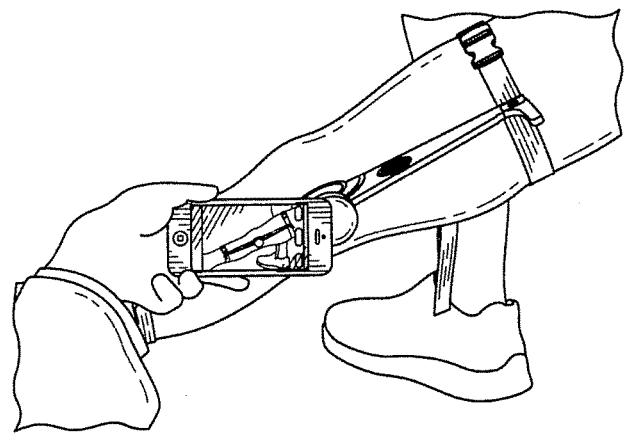
Figure 11:
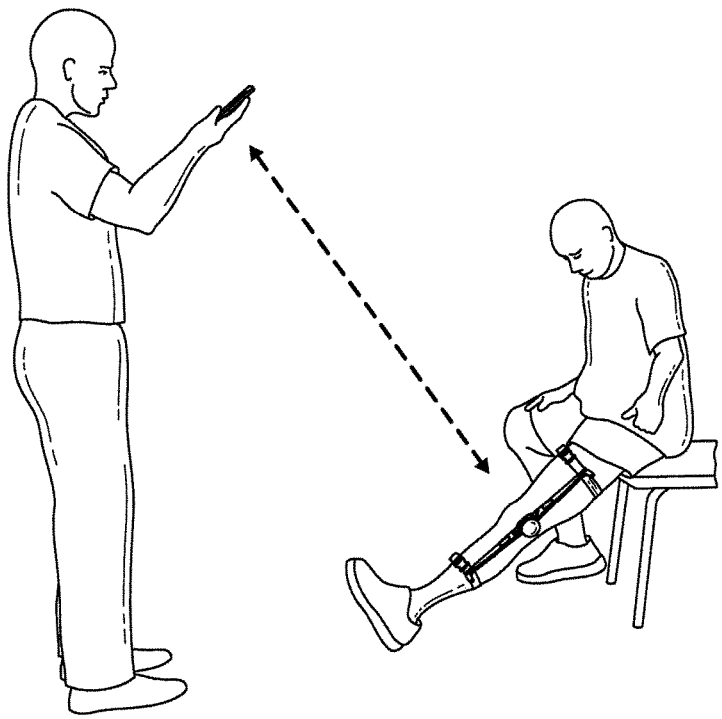
Figure 13:
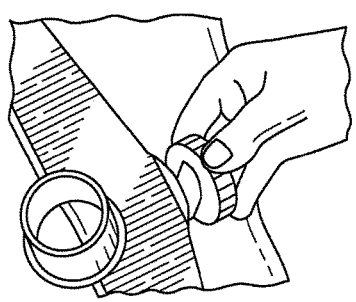

The steps for performance of the method of the present invention will now be explained with reference to FIGS. 7-19. Initially, a patient is seated on the edge of a chair with his/her leg held straight out at full extension with the heel of the foot on the floor and the toes pointing up and slightly dorsiflexed (no toe out). In this regard, it is noted that flexion of over 10° can prevent use of the IAG. In this position, the IAG is either held against the lateral side of the leg by the patient with the aid of the support arms 15, or can be attached to the leg of the patient using a pair of straps, for example, as shown in FIGS. 7 & 10. As shown in FIGS. 7 & 8, the IAG is positioned at the midline of the leg with the focal angle tube 5 face up and approximately ¼" inward from the side of the knee at the anterior/posterior midline of the thigh, knee and calf with bubble of the bubble level 9 centered as shown in FIG. 9, but some slight displacement of the bubble from the fully centered position is acceptable.

Figure 12:
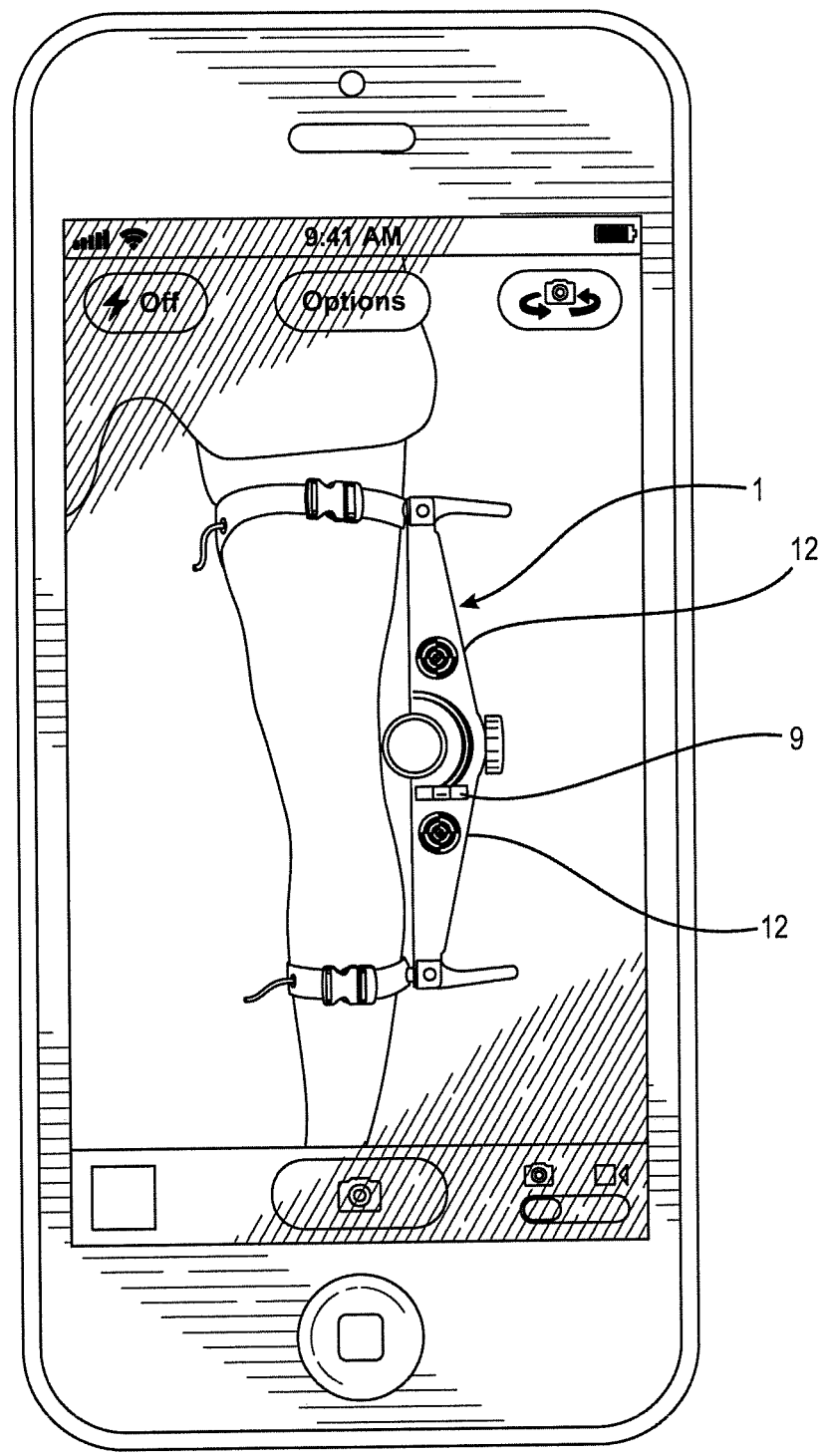

At this point in the method, a low angle side view image is taken at the midline of the leg that shows the full length of the IAG. In preparation of a second frontal image, the tape measure 7 is extended to a predetermined distance, e.g., four feet. With the camera or smart phone at the end of the tape measure (FIG. 11), standing directly in front of the patient's foot, looking down at the IAG, the camera position is adjusted so that only the rim of the focal angle tube 5 is visible and not any of its interior; for this purpose, it is helpful if the interior of the tube has a distinctively different coloration from that of the rim. The focusing element(s) 12 (one as in FIG. 1, but preferably two as shown in FIG. 12) are used to insure that a clear picture is obtained and that the camera or smart phone is aimed straight on the focus angle tube 5. An image of the image alignment guide attached to the leg of a patient is then taken such as that shown in FIG. 12, and preferably two or three are taken so that the brace manufacturer can choose the best image. In this regard, the image should be examined to insure that there is no toe out, the bubble appears centered and only the rim of the focus angle tube 5 appears.

Figure 14:
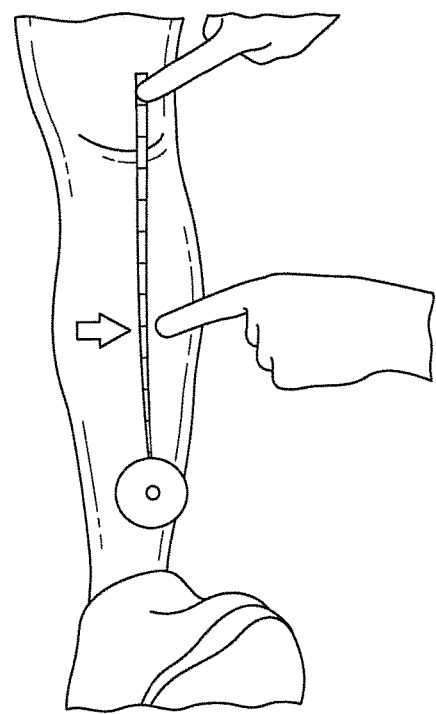

After satisfied with the frontal image(s), the tape measure 7 can be removed (FIG. 13) and used to measure the distance from the center of the patella to a position on the shin bone that corresponds with the length of the tibia shell of the brace to be ordered, as shown in FIG. 14; of course, a separate tape measure could be used instead of disconnecting the tape measure 7.

Figure 15:
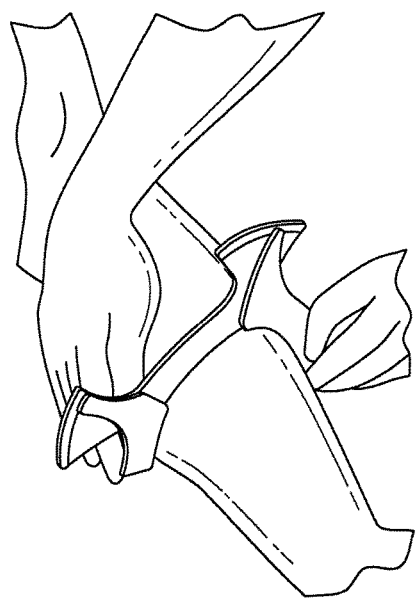
Figure 16:
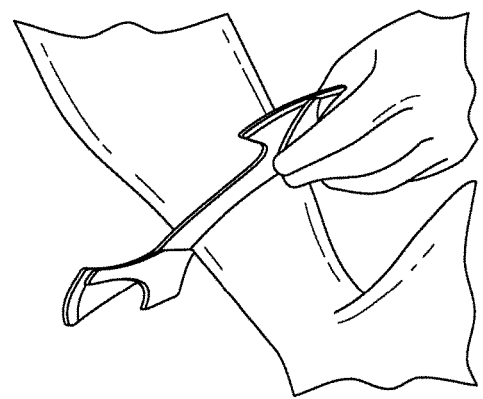

At this point, the tibial contour gauge 16 is applied at a position 6-8" below the patella, centered on the crest of the tibia. The alignment arms 16a, 16b are then adjusted until the gauge 16 is in full contact with the medial and lateral contour of the shin with no gapping (FIG. 15). The gauge is then moved down toward the ankle (FIG. 16) and removed without changing the position of the alignment arms 16a, 16b so that the numbers on the scales 16d can be read off (FIG. 17) and recorded.

Figure 18:
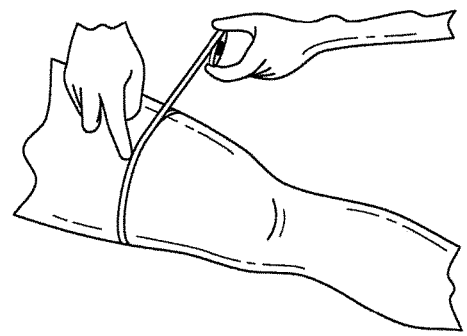
Figure 17:
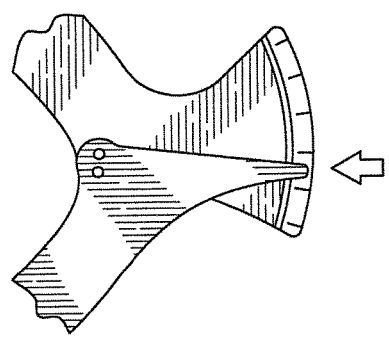
Figure 19:
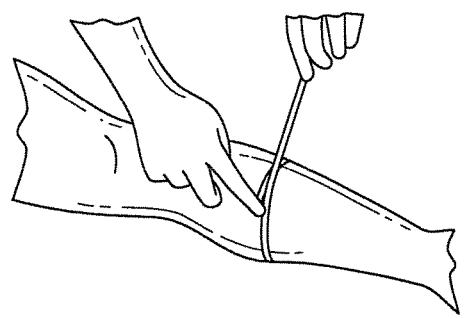
Figure 20:
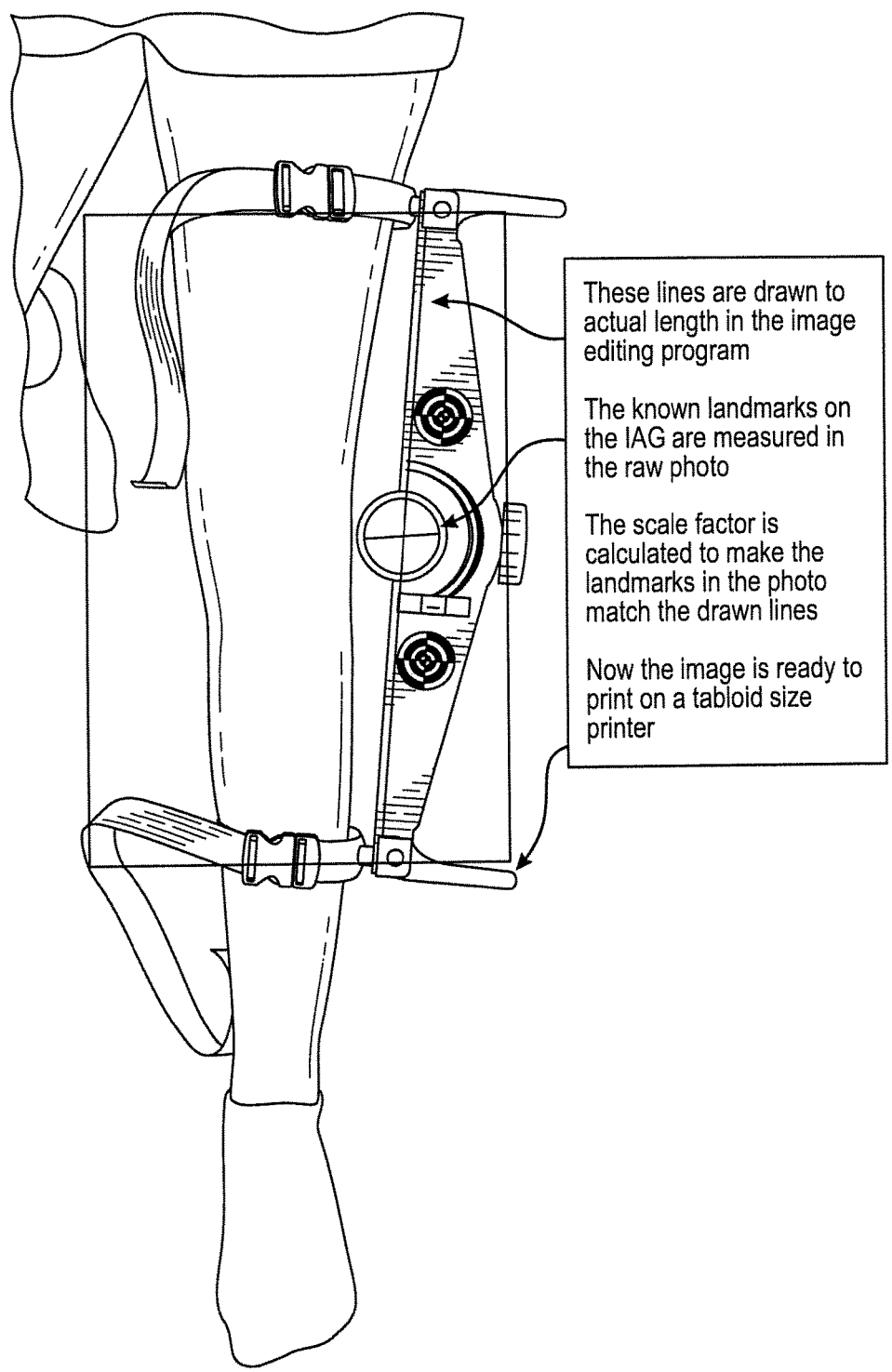
FIGS. 20-25 show steps in a method of producing a custom knee brace using an image produced in accordance with the present invention.

As shown in FIGS. 18 & 19, after removal of the tibial contour gauge 16, four circumferential measurements of the leg, about 3" and 7" above and below the knee center are taken and recorded along with the associated distance at which each was obtained. Of course, these measurements could be taken at a different point in the process, such as between the measurement step of FIG. 15 and use of the tibial contour gauge 16.

The images, readings and measurements obtained can be easily transmitted electronically to the brace manufacturer, or can be recorded on a conventional electronic medium, such as a CD, DVD or the like and mailed to the brace manufacturer. With the aid of this information as well as the dimensions visible on the ruler arms 11 in the frontal image, the brace manufacture will have all of the data required for inputting into the software of a 3D printer for producing of a knee brace that is custom fit for the particular patient's leg with a high degree of accuracy.

However, as noted above, until the costs of suitable 3D printers becomes such as to make their use commercially feasible for producing custom knee braces, the present invention will find current utility in the production of custom knee braces using malleable aluminum bands to create leg form on which graphite pre-preg is applied and cured. FIGS. 20-24 show steps in one such method.

Figure 21:
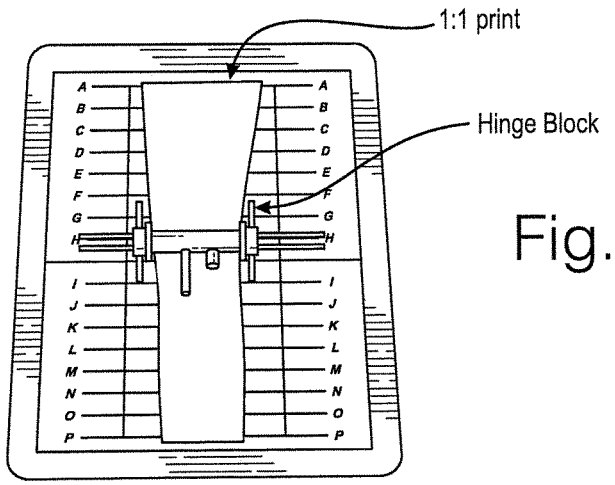
Figure 22:
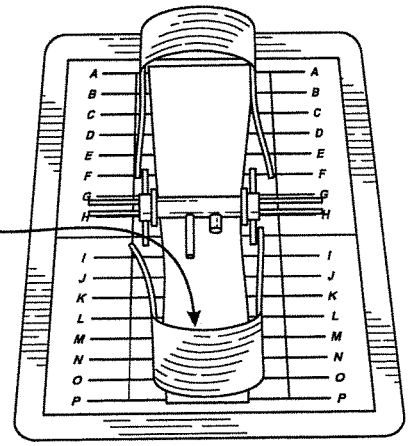
Figure 23:
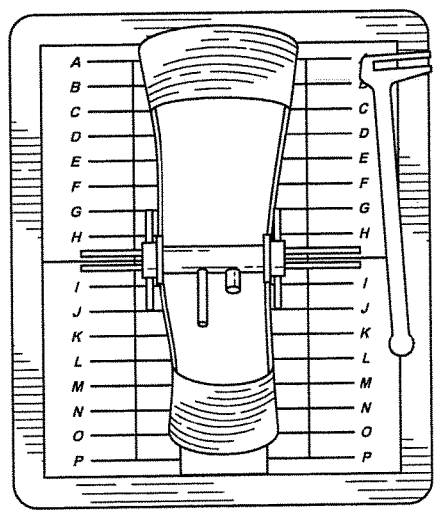
Figure 24:
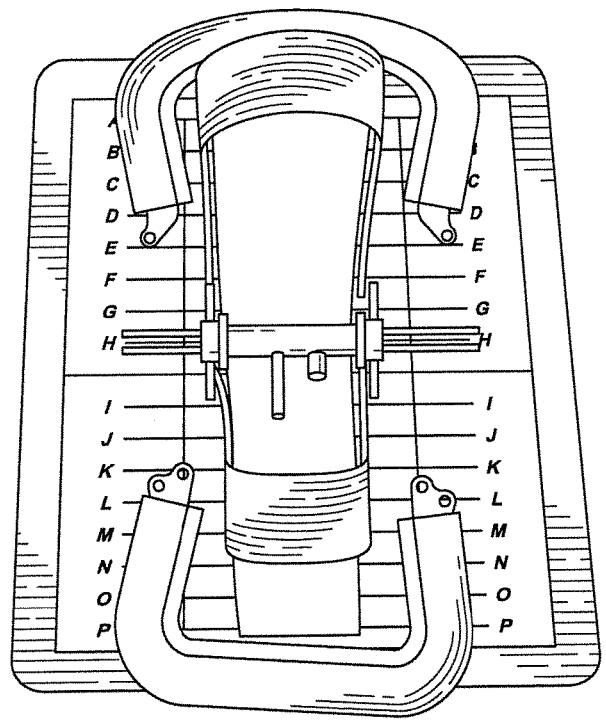
Figure 25:
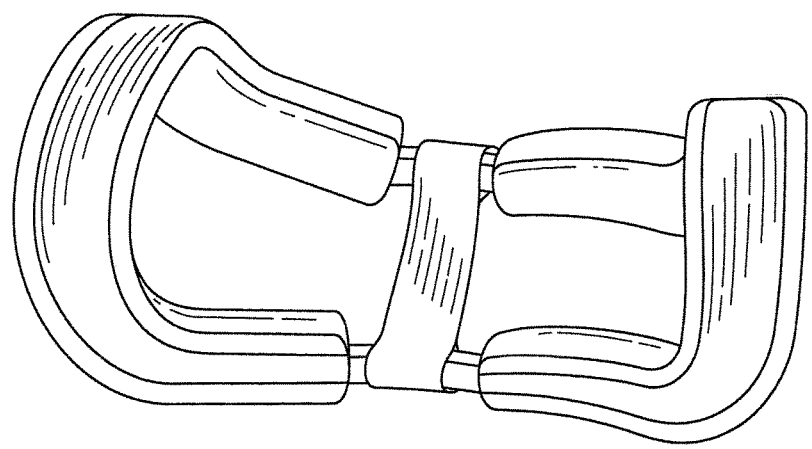

With reference to FIGS. 20-24, first, using known landmarks on the IAG, a scale factor is determined (FIG. 20) and the image printed in actual (1:1 scale) size, and the full size image is then put on a layout board (FIG. 21). Using the circumferential measurements, the correct malleable aluminum bands to create a leg form are determined (FIG. 22). Malleable aluminum bands are then formed to the 1:1 image and inserted into the hinge blocks (FIG. 23). The pre-bent joints are then removed from the joint blocks and are inserted into uncured pre-preg graphite and which is surrounded with a flexible silicone mold (FIG. 24). The uncured pre-preg wrapped in the flexible silicone mold is applied over the formed aluminum shells, a vacuum bag is put over the entire assembly and it is put into an oven to cure the pre-preg (FIG. 25). Once in the oven, the vacuum bag holds the silicone mold tightly to the formed aluminum bands. The silicone mold expands and creates the compression that is needed to insure structurally sound cuff pieces. The mold also creates the space where the pads will fit.

After the curing process, the silicone molds are removed and the cured pre-preg bands, with the joints bonded in, are removed from the joint block. The cured graphite bands are smoothed and painted. The joints are assembled, straps and pads added and the custom brace is ready to deliver to the patient.

The above method of production should be viewed solely as an example of one custom knee brace manufacturing process, and various others will be apparent to those of ordinary skill, especially given that different knee brace designs may require other, additional or different steps to be employed.

As will be apparent, the method in accordance with the present invention allows for the possibility of brace manufacture being commenced the same day as the patient's visit to the prescribing doctor if electronic transmission is used to send images, readings and measurements to the brace manufacturer, as well as reducing the costs that would otherwise be associated with producing and shipping a negative cast and using the cast to make a model of the patient's leg.

What is claimed is:
1. An image alignment guide for producing images suitable for use in producing of a knee brace, comprising:
   an arm that carries a focal angle tube for use in setting the angle of a camera relative to the leg of a patient,
   means for fitting the arm against the lateral side of both the femur and tibia of the leg of the patient with the focal angle tube extending from the arm in anterior direction at the anterior/posterior midline of the thigh, knee and calf, and means for indicating the level of the arm relative to a horizontal plane when positioned against the side of the leg of the patient.

2. Method of preparing an image for use in producing of a custom knee brace, comprising the steps:

placing an image alignment guide having an arm that carries a focal angle tube, for use in setting the angle of a camera relative to the arm, against the lateral side of both the femur and tibia of a patient's leg at an anterior-posterior mid-line of the leg and with the focal angle tube facing in an anterior direction at the side of the knee, taking a low angle side view digital image showing the full length of image alignment guide on the patient's leg, taking a frontal digital image at a measured distance from the leg with the focal angle tube aligned with only the rim of the focal angle tube visible, measuring the length of the patient's leg from the center of the patella to a position on the leg at which a shell of a brace to be produced for the patient is to be located, measuring the crest of the tibia using a tibial contour guide comprising two indicator parts each of which has a pointer and each of which is pivotably mounted on a respective end portion of a gauge part that carries a respective scale for co-acting with the pointer on each of indicator parts, wherein an inner contour of the guide formed by the indicator parts and gauge part is configured for circumferentially fitting around the patient's leg on the tibial crest with no gaps between the inner contour of the guide and the patient's leg, measuring the circumference of the patient's leg at locations about 3 and 7 inches above and below the center of the knee, and sending all images, readings and measurements obtained to a knee brace manufacturer for use in producing of a knee brace for the patient.

\* \* \* \* \*